United States Patent [19]

Lomask

[11] Patent Number: 5,379,777
[45] Date of Patent: Jan. 10, 1995

[54] WHOLE BODY PLETHYSMOGRAPH FOR NON-INVASIVE PULMONARY MEASUREMENTS OF UNRESTRAINED SMALL ANIMALS

[75] Inventor: Morton Lomask, Sharon, Conn.

[73] Assignee: Buxco Electronics, Inc., Sharon, Conn.

[21] Appl. No.: 178,964

[22] Filed: Jan. 7, 1994

[51] Int. Cl.⁶ ............................................. A61B 5/08
[52] U.S. Cl. ..................................... 128/716; 119/15; 128/200.14
[58] Field of Search ............. 128/716, 203.12, 200.14; 119/15, 17, 18, 19

[56] References Cited

U.S. PATENT DOCUMENTS

| | | | |
|---|---|---|---|
| 4,305,347 | 12/1981 | Hemenway et al. | 119/15 |
| 4,479,493 | 10/1984 | Bung et al. | 119/15 |
| 4,520,808 | 6/1985 | LeBauve | 128/200.14 |
| 4,781,146 | 11/1988 | Spengler | 119/15 |
| 4,841,982 | 6/1989 | Nikiforov et al. | 128/716 |
| 4,917,048 | 4/1990 | Spengler | 119/15 |
| 5,109,797 | 5/1992 | Briant et al. | 128/200.14 |
| 5,156,776 | 10/1992 | Loedding et al. | 128/203.12 |

Primary Examiner—William E. Kamm
Assistant Examiner—Bria M. Green
Attorney, Agent, or Firm—Salter & Michaelson

[57] ABSTRACT

A whole body plethysmograph for pulmonary measurements of unrestrained small animals includes a cylindrical animal chamber and an integral reference chamber. The animal chamber and the reference chamber each include ports for receiving transducer nipples. The animal chamber and the reference chambers also include ports for selectively venting each of the chambers. A port is mounted in a bulkhead which separates the animal chamber and the reference chamber, and a length of tubing extends from the valve into the reference chamber for providing a high resistance bleed path between the animal chamber and the reference chamber. The plethysmograph further includes an aerosol manifold in the top of the animal chamber. The aerosol manifold includes a plurality of radially extending apertures for uniformly distributing the aerosol in the animal chamber. The plethysmograph still further includes two pneumotachographs in the top of the animal chamber. The plethysmograph may be used either as a volume device or a flow device. However, the preferred method of use is as a flow device.

12 Claims, 3 Drawing Sheets

WHOLE BODY PLETHYSMOGRAPH FOR NON-INVASIVE PULMONARY MEASUREMENTS OF UNRESTRAINED SMALL ANIMALS

BACKGROUND AND SUMMARY OF THE INVENTION

The instant invention relates to laboratory testing devices, and more particularly to a whole body plethysmograph for use in making non-invasive pulmonary measurements of unrestrained small animals.

Whole body plethysmographs for non-invasive pulmonary measurements of small animals have heretofore been known in the art. For example, a biased-flow, whole body plethysmograph is described in an article "Aeroallergen-induced dyspnea in freely moving guinea pigs; quantitative measurement by bias-flow ventilated whole body plethysmography", by N. Chand et al, Allergy 1993: 48:230–235, Munksgaard 1993. The whole body plethysmograph illustrated on Page 231 of the article comprises a rectangular box having a bias flow inlet, a bias flow outlet, a transducer port, a reference bottle, and a water bottle. The reference bottle is connected to the rectangular box by a length of tubing and it is further vented to atmosphere by a length of tubing.

One particular shortcoming of the prior art plethysmographs is that the animal chambers have rectangular or other odd shapes. It has been found that these odd shapes do not promote uniform distribution of the aerosol injected into the interior of the box during testing. Still further, the aerosol injection devices of the prior art have not been found to be effective for evenly distributing the aerosol throughout the animal chamber. Accordingly, there are often uneven concentrations of aerosol which settle in the corners of the boxes. Another shortcoming of the prior art devices is that the reference chambers are separate from the animal chamber. It has been found that maintaining separate animal reference chambers introduces temperature, pressure, and ambient noise differences into the measurements which could affect the results of the testing.

The instant invention provides an improved plethysmograph comprising a cylindrical animal chamber and an integral reference chamber. The animal chamber and the reference chamber are provided in a cylindrical container wherein an internal bulkhead wall separates the two chambers. The reference chamber is situated above the animal chamber. The animal chamber and the reference chamber include ports for receiving differential pressure transducer leads. The animal chamber and the reference chambers also include ports for selectively venting each of the chambers. A port is provided in the bulkhead wall and a length of high resistance tubing is connected to the port for providing a high resistance bleed path between the animal chamber and the reference chamber. The plethysmograph further includes an aerosol manifold which extends into the top of the animal chamber. The aerosol manifold includes a plurality of radially extending apertures which open into the animal chamber for evenly distributing the aerosol in the animal chamber. The radial apertures essentially act as a showerhead for distributing the aerosol in the animal chamber. The plethysmograph still further includes two pneumotachographs in the top of the animal chamber for creating a pressure drop in the animal chamber during respirations. The plethysmograph may be used either in a volume mode of operation by plugging the pneumotachographs, or in a flow mode of operation by leaving the pneumotachographs unplugged. However, the preferred method of use is as a flow device. In the flow mode of operation, the air flows into the animal chamber through the pneumotachographs and outwardly through the multiple ports to a negative pressure reservoir via high-resistance tubing.

Accordingly, it is an object of the instant invention to provide a whole body plethysmograph for non-invasive pulmonary measurement of unrestrained small animals.

It is another object to provide a plethysmograph having a circular or cylindrical animal chamber.

It is still another object to provide a plethysmograph having a reference chamber integrally formed with the animal chamber.

It is a further object to provide a plethysmograph which can function either in a volume mode of operation or in a flow mode of operation.

It is yet object to provide an aerosol manifold having a plurality of apertures for evenly distributing aerosol in the animal chamber.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE PREFERRED EMBODIMENT

Figure 1:
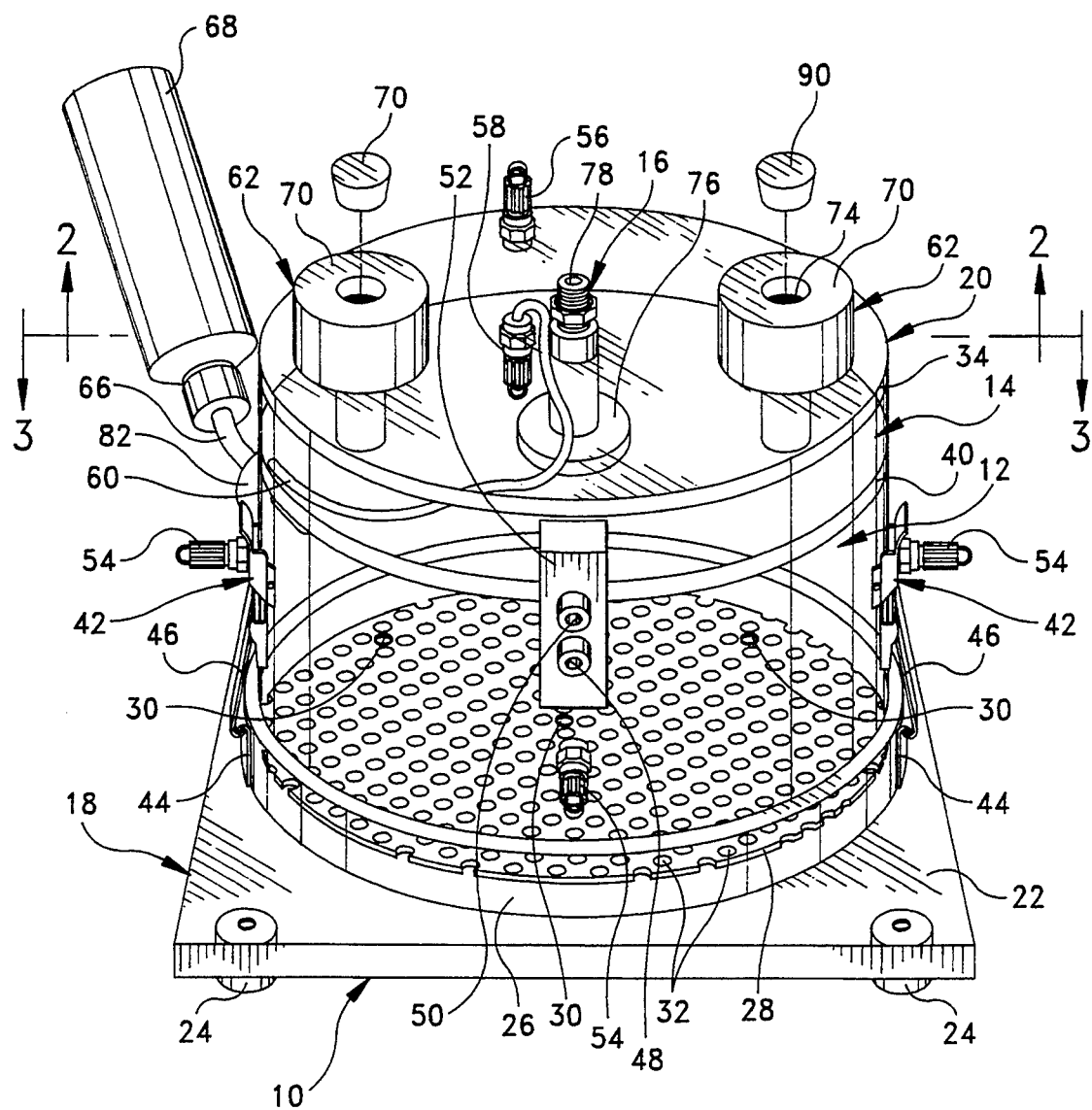
FIG. 1 is a perspective view of the instant plethysmograph.
Figure 2:
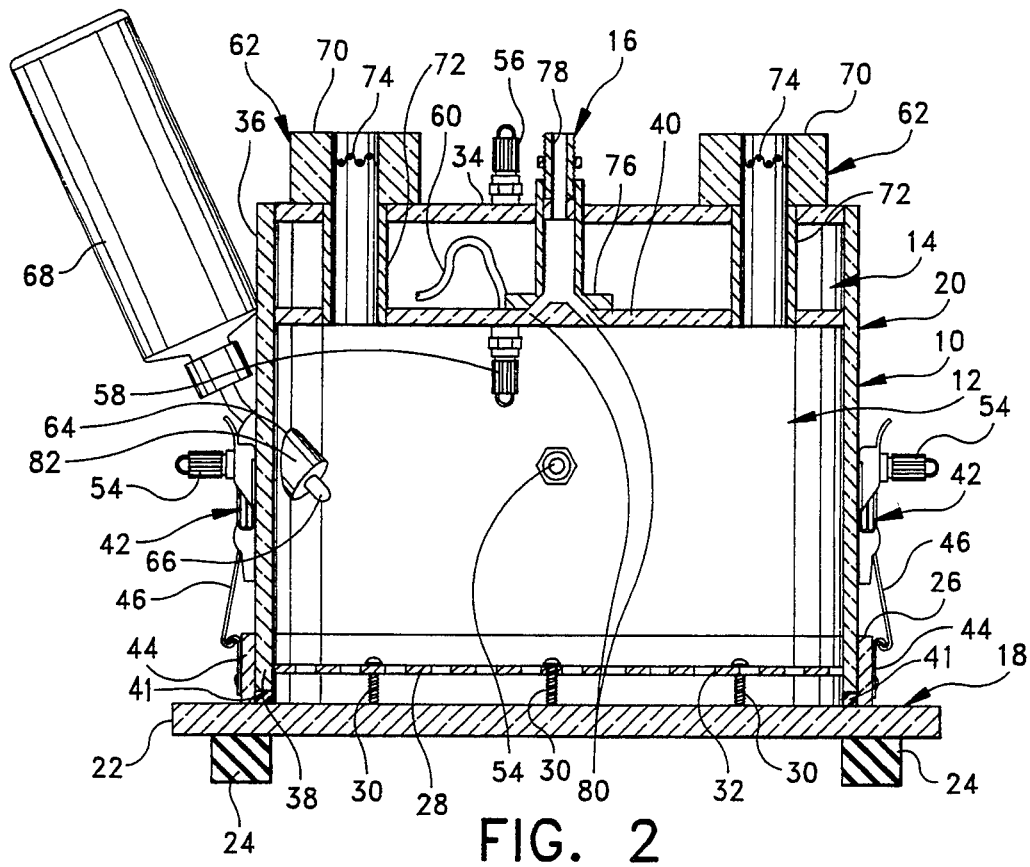
FIG. 2 is a cross-sectional view thereof taken along line 2—2 of FIG. 1.
Figure 3:
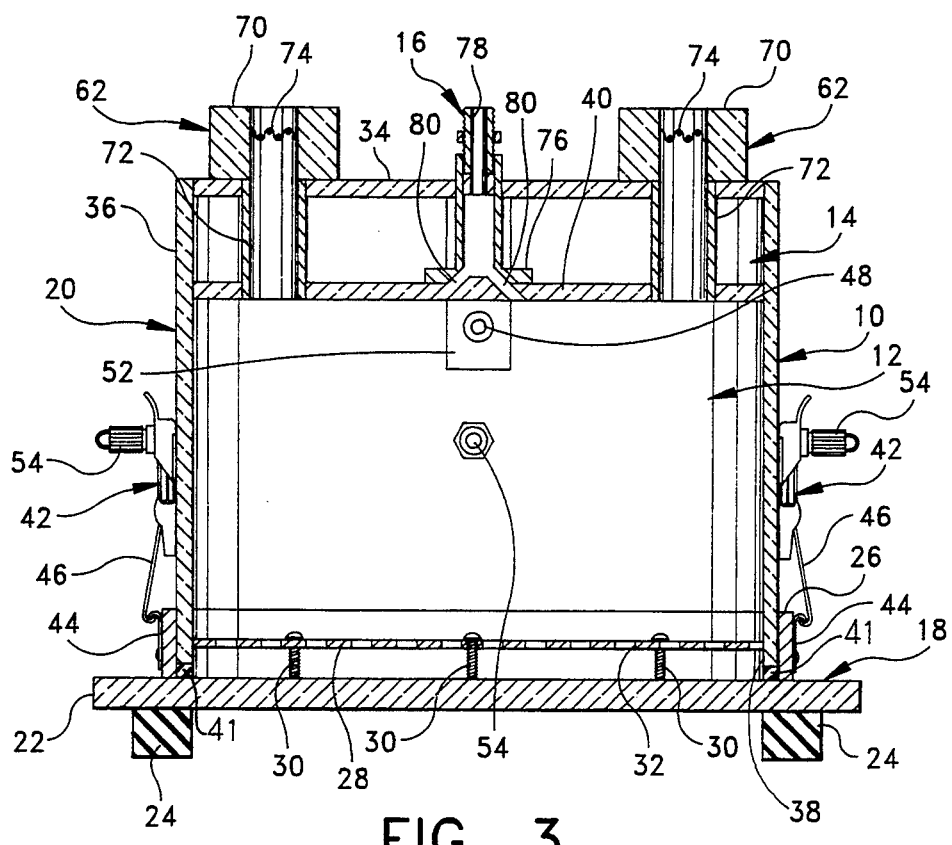
FIG. 3 is another cross-sectional view thereof taken along line 3—3 of FIG. 1.

Referring now to the drawings, the plethysmograph of the instant invention is illustrated and generally indicated at 10 in FIGS. 1–3. As will hereinafter be more fully described, the instant plethysmograph includes a cylindrical animal chamber generally indicated at 12, an integral reference chamber generally indicated at 14, and a showerhead-type aerosol manifold generally indicated at 16 for evenly distributing an aerosol in the animal chamber 12. The instant plethysmograph 10 generally comprises a base portion generally indicated at 18, and a cover portion generally indicated at 20 which is received onto the base portion 18. The base portion 18 and cover portion 20 are received together, wherein they cooperate to define the animal chamber 12 and the integral reference chamber 14. The base portion 18 and cover portion 20 are preferably constructed from clear plexiglass or any other suitable clear plastic material so that the animal being tested can be viewed during testing. The base portion 18 comprises a base plate 22, a plurality of feet 24 mounted to a lower side of the base plate 22, and an upright cylindrical wall 26 affixed to an upper side of the base plate 22. A circular floor panel 28 is positioned inside the cylindrical wall 26 and it is maintained in spaced relation above the upper side of the base plate 22 by a plurality of screws 30 which extend downwardly through the floor panel 28. The floor panel 28 includes a plurality of apertures 32 so that during long term measurements animal excrement may fall through the floor panel 28 onto the upper surface of the base plate 22. This enables the animal chamber 12 to remain relatively clean during the testing process. The cover portion 20 of the plethysmograph 10 comprises a cylindrical container having a top wall 34, a side wall 36, an open bottom 38, and a bulkhead wall 40 positioned in spaced adjacent relation to the top wall 34. In this connection, the top wall 34, side wall 36 and bulkhead 40 of the cover 20 define the reference chamber 14 of the device 10. The cover 20 is received onto the base 18 wherein the open bottom 38 is received inside the upright cylindrical wall 26 and over the floor panel 28 so that the bottom 38 rests on the base plate 22 of the base portion 18. A rubber gasket 41 is positioned inside the upright wall 26 to provide a tight, engaging, air tight fit when the cover portion 20 is received onto the base 18. In this connection, the bulkhead 40 and side wall 36 of the cover portion 20 and the base plate 22 of the base portion 18 cooperate to define the animal chamber 12 of the device 10. The volume enclosed by the animal chamber 12 is approximately 1000 times the tidal volume of the animal being tested. The cover portion 20 and base portion 18 are releasably retained in engaging relation by means of two conventional hinged clamps generally indicated at 42 which are mounted on opposite sides of the device 10. More specifically, the clamps 42 each comprise a securing plate 44 mounted to the upright cylindrical wall 26 and a hinged arm 46 which is mounted to the side wall 36 of the cover portion 20. In use, a small animal, such as a guinea pig is placed on the floor panel 28 of the base 18 and the cover portion 20 is received over the base portion 18 and clamped in position to enclose the animal in the animal chamber 12.

The animal chamber 12 and the reference chamber 14 each include a port, 48 and 50 respectively, for receiving a sensor nipple (not shown) of a differential pressure transducer (not shown). The two transducer ports 48 and 50 respectively, are positioned in the side wall 36 of the cover portion 20 immediately above and below the bulkhead 40 separating the two chambers 12 and 14, and they extend through a rectangular appendage 52 mounted to the side wall 36 of the cover portion 20. The animal chamber and the reference chamber further include a plurality of ports for selectively venting the respective chambers 12 and 14. In this connection, the animal chamber 12 includes ports 54 which are circumferentially spaced around the side wall 36 and the reference chamber 14 includes a single port 56 in the top wall 34 of the cover portion 20. It is noted that the ports 54 in the animal chamber 12 are utilized to apply a bias-flow through the animal chamber 12 so that the animal does rebreathe the chamber air over and over again causing depletion of oxygen and build-up of carbon-dioxide. A more detailed description of the bias-flow will be provided hereinafter in connection with use of the device 10.

A port 58 is also provided in the bulkhead 40 and a length of high-resistance tubing 60 is connected to the port 58 to provide a high-resistance bleed path between the animal chamber 12 and the reference chamber 14. More specifically, a first end of the port 58 is in communication with the animal chamber 12 and a second end of the port 58 is in communication with the reference chamber 14. The length of high-resistance tubing 60 is attached to the second end of the valve 58 so that it extends into the interior of the reference chamber 14. The ports 54, 56 and 58 of the type contemplated herein, are conventional in the art, and they are movable between open and closed positions.

The plethysmograph 10 still further includes two pneumotachographs generally indicated at 62, and a port 64 (FIG. 2) in the side wall 36 of the animal chamber 12 for receiving the spigot 66 of a water bottle 68. When bias flow is applied to the animal 12, the two pneumotachographs 62 are essentially intake ports for the animal chamber 12, and they are radially aligned with two opposing ports 54 in the animal chamber 12. Each pneumotachograph 62 comprises an annular body 70 mounted on top of the cover portion 20 and a tubular shaft 72 which extends downwardly from the annular body 70 through the reference chamber 14 and into the top of the animal chamber 12, i.e. into the bulkhead 40. The annular body 70 of each pneumotachograph 62 includes a fine-mesh screen 74 extending across the central opening therein. The screen 74 restricts the flow of air into and out of out of the animal chamber 12 and thereby creates a pressure drop in the animal chamber 12. This pressure drop is measured by a transducer lead (not shown) mounted in the transducer port 48 in the animal chamber 12.

The aerosol manifold 16 is centrally located on top of the cover portion 20 and it is operative for distributing an aerosol into the animal chamber 12. The aerosol manifold 16 extends downwardly through the reference chamber 14 where an internal end 76 communicates with the animal chamber 12 for distributing the aerosol therein. An external end 78 of the manifold 16 receives an aerosol from an aerosol source, and the internal end 76 of the port 16 branches into a plurality of radially extending apertures 80 which open into the animal chamber 12 for evenly distributing the aerosol throughout the animal chamber 12. The plurality of radial apertures 80 essentially act as a showerhead for evenly distributing the aerosol, and since the animal chamber 12 is round in configuration, there are no corners or pockets in which uneven concentrations of the aerosol can settle. When the aerosol manifold 16 is not in use, a stopcock (not shown) seals the external end 78.

The port 64 for the spigot 66 of the water bottle 68 is conventional in construction, and it comprises an annular rubber stopper 82 through which the spigot 66 of the water bottle 68 is received. By providing the animal with water during testing, long term measurements may be obtained without opening the device 10.

In use, the instant plethysmograph 10 is operable either in a volume mode, or in a flow mode. The preferred method of use is in a flow mode.

In the preferred method of use, i.e. as a flow device, the pneumotachographs 62 are open. Since the animal chamber 12 receives atmospheric fluctuations and noise through the open pneumotachographs 62, it is desirable that the reference chamber 14 be subject to the same conditions. Accordingly, the port 56 in the reference chamber 14 is open to vent the reference chamber 14 to atmosphere. The high resistance bleed path, between the chambers 12 and 14, i.e. the port 58, is closed. The ports 54 in the animal chamber 12 are opened and they are principally operable for drawing a bias air flow through the animal chamber 12 to keep the animal from rebreathing chamber air during long term measurements, and for drawing off aerosol exposures. In this regard the ports 54 are connected to a negative pressure reservoir (not shown) through high-resistance tubing (not shown). In the flow mode of operation, air flows into the animal chamber 12 through the pneumotachographs 62, and outwardly through the multiple ports 54, through the high-resistance tubing to the negative pressure reservoir. As the animal breathes during testing, the pneumotachographs 62, or more specifically, the screens 74 in the pneumotachographs 62, restrict the flow of air into and out of the animal chamber 12 and thereby create a small pressure drop in the animal chamber 12. The pressure drop inside the animal chamber 12 and the pressure in the reference chamber 14 are measured using a differential pressure transducer (not shown) connected to a preamplifier (not shown). One sensor nipple (+) of the transducer is attached to the port 48 in the animal chamber 12 while the other sensor nipple (−) is attached to the port 50 in the reference chamber. The differential pressure transducer subtracts the reference chamber signal from the animal chamber signal to produce a respiration signal representing a respiration pattern of the animal. The high-resistance tubing between the animal chamber and the negative reservoir of the bias-flow supply will not short circuit or compete significantly with the resistance of the pneumotachographs 62, which are performing the respiratory measurements. Thus, the pneumotachographs 62 may continue measurements while the bias-flow is operating. The distribution of the vent ports 54 about the circumference of the cylindrical animal chamber 12, and their symmetrical relationship to the two pneumotachographs 62 on the top wall, provide a uniform gas concentration within the animal chamber 12.

Figure 4A:
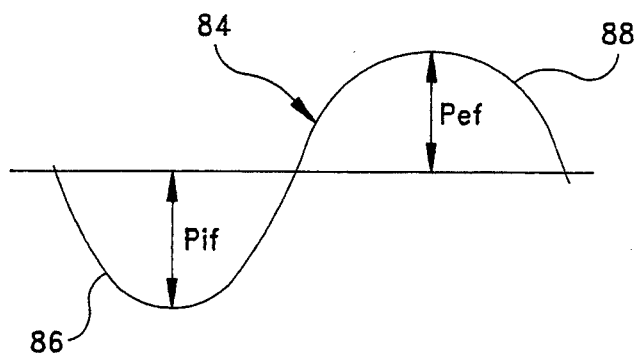
FIGS. 4a and 4b are graphical illustrations of waveforms generated from the plethysmograph.
Figure 4B:
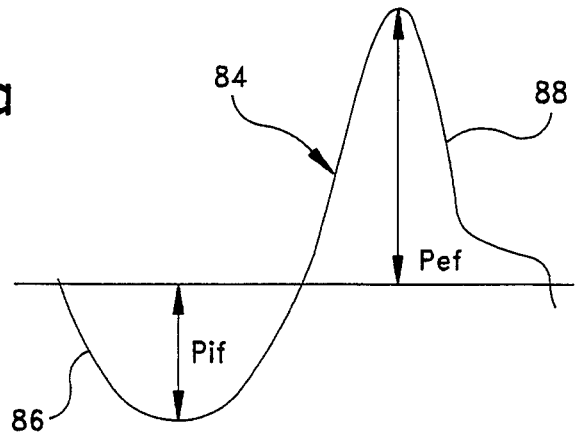

The respiration signal obtained during flow testing represents the difference between the flow caused by thoracic movement and the nasal flow. The respiration signal is amplified through the preamplifier to produce a waveform generally indicated at 84 as illustrated in FIGS. 4a and 4b. The waveform 84 includes a first portion 86 representing inspiration of the animal and a second portion 88 representing expiration of the animal. When there is no broncho-constriction, i.e. during normal respiration, the thoracic flow and nasal flow are almost exactly out of phase (FIG. 4a), and the thoracic flow is slightly greater, on the order of 10% greater than the nasal flow due to heating of the air on entry into the animal and the addition of water vapor. When there is broncho-constriction, i.e. after addition of an aerosol to the animal chamber, the nasal flow lags behind the thoracic flow, and thus the substraction of the two is not as complete as before (FIG. 4b). The resulting plethysmograph waveform in FIG. 4b is no longer representative of the true flow into and out of the animal, however for the purposes of explanation it will continue to be called a pseudo-flow signal. Under severe broncho-constriction, the magnitude of the thoracic flow increases; and the nasal flow decreases; and the nasal flow lags behind the thoracic flow. This makes the signal, which is based on a subtraction of the two flows, larger. The principles for analysis of the waveform 84 are as follows: (1) During broncho-constriction, the "expiratory" flow signal becomes punctate in early expiration, falling off in later expiration (FIGS. 4b and 5b). This due to the phase shift developing between the nasal and thoracic components. Thus, more air appears to be expelled in early expiration, and less in late expiration. (2) During broncho-constriction, the respective amplitudes Pif and Pef (FIG. 4a and 4b) of the "inspiratory" and "expiratory" phases increase. However, the expiratory amplitude Pef seems to increase more than the inspiratory amplitude Pif, apparently due to the expiratory effort being required to expel the air.

Figure 5A:
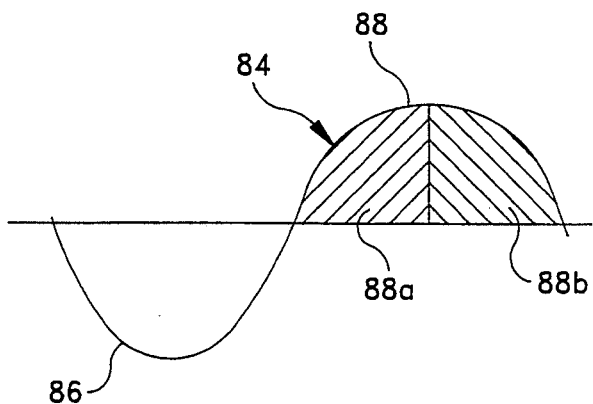
FIGS. 5a and 5b are graphical illustrations of a method for analyzing the waveforms generated from the plethysmograph.
Figure 5B:
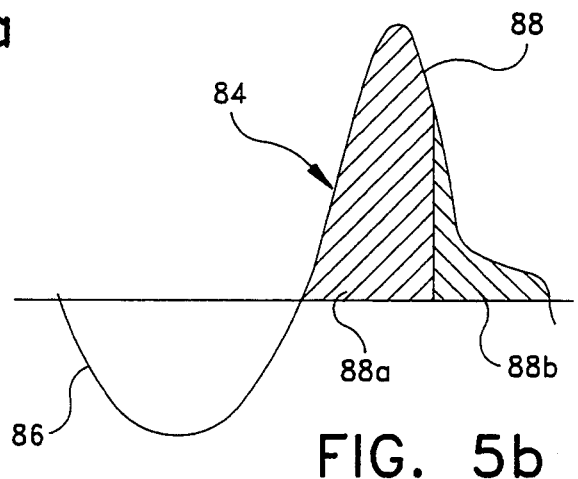

Referring now to FIGS. 5a and 5b, the expiration region 88 is divided into two regions, based on expired volume; the first 60% of the expiration 88a, and the last 40% of the expiration 88b. The average flow during the first 60% of the expiration 88a, divided by the average flow during the last 40% of the expiration 88b produces a ratio designated as PAUSE. The PAUSE ratio is a measure of the shape of the expiration side 88 of the waveform 84, whether it is pushed to early expiration and to what degree. The PAUSE ratio is of two flows; and therefore it is dimensionless. Accordingly, to compute PAUSE, the flow signal does not need to be calibrated.

By utilizing the fact that the expiration amplitude Pef increases more than the inspiration amplitude Pif during constriction, the PAUSE parameter can be enhanced. In this connection, the amplitude Pef on the expiration side of the waveform is divided by the amplitude Pif on the inspiration side to produce an amplitude ratio parameter (Pef/Pif). To obtain an enhanced PAUSE value, PENH, the PAUSE value is multiplied by the amplitude ratio parameter. The amplitude ratio parameter increases the sensitivity in observing a constriction by a factor of 2 to 3 times.

When used as a volume device, the pneumotachographs 62 are plugged with rubber stoppers 90. A bias-flow ventilation draws air into the animal chamber 12 from atmosphere through high-resistance tubing connected to a pair of ports 54 on opposite sides of the chamber 12, and outwardly from the animal chamber 12 through the remaining pair of opposite ports 54 through high pressure tubing to the negative pressure reservoir. The relationship of the inlet and outlet ports along the circumference of the cylindrical chamber 12 are symmetrical. In this way concentration within the chamber 12 is kept uniform. If the time constant of the chamber volume and the resistance of the tubing is greater than 5 seconds (large compared to the respiration cycle of a small animal), then the pressure fluctuations within the chamber 12 due to respiration will not be compromised. The port 58 between the animal chamber 12 and the reference chamber 14 is opened to provide a high resistance bleed path. Changes in animal chamber 12 pressure (P) represent volume changes due to respirations (inspiration/expiration) of the animal. Since the pressure inside the animal chamber 12 may fluctuate, or the ambient environment may fluctuate, i.e. noise, the pressure measurements inside the animal chamber 12 are taken relative to the reference chamber 14. The differential pressure transducer subtracts the signal in the reference chamber 14 from the signals in the animal chamber 12. In this way, ambient noise and pressure fluctuations are subtracted from the animal signal. The resulting signal from the differential pressure transducer is differentiated to generate a pseudo-flow signal. The pseudo-flow signal is proportional to the difference between the rate of changes of the thoracic volume and the nasal flow. The difference indicates the flow rate when the animal is not constricted. However, when the animal is constricted, the pseudo-flow signal no longer indicates flow rate. During constriction, or dyspnea, the shape of the waveform 84 changes and the degree of dyspnea is determined using the parameters as described above. Since the parameters are based on the shape of the waveform 84 rather than its amplitude, the measure of dyspnea does not require calibration of the transducers and preamplifiers.

It is pointed out that use of the plethysmograph 12 as a flow chamber is preferred for the following reasons. Measurements taken during use as a volume chamber are subject to leaks. In use as a flow device, the pneumotachographs 62 are open to atmosphere, and thus constitute large leaks. Use of the plethysmograph 10 as a flow chamber offers the opportunity to continue pulmonary measurements during aerosolization because there is only a small pressure build up in the animal chamber 12 due to introduction of the aerosol. Since computation of the flow parameters are performed on the flow signal, it is more convenient that the flow is available directly, rather than converted from a volume signal through a differentiator.

It can therefore be seen that the instant invention provides an effective whole body plethysmograph 12 for making pulmonary measurements of small animals. The plethysmograph 10 is designed to be used either as a flow chamber or a volume chamber, and it is further designed to accommodate small animals for long term measurements, i.e. 24 hours or longer. In this connection, the animal chamber 12 includes a port 64 for a water bottle 68, and multiple ports 54 for ventilation during use. During use as a flow chamber, the animal chamber 12 is open to atmosphere through the pneumotachograph screens. The aerosol port 16 is designed with a showerhead arrangement of apertures 80 so even manner throughout the animal chamber 12. Since the shape of the animal chamber 12 is cylindrical, there are no corners which can create regions of non-uniform aerosol concentration. For these reasons, the instant invention is believed to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

I claim:

1. A whole body plethysmograph comprising:
   a generally cylindrical animal chamber;
   a port in said animal chamber for receiving a transducer lead therein;
   means for selectively venting said animal chamber to atmosphere;
   a reference chamber in closely spaced adjacent relation to said animal chamber;
   a port in said reference chamber for receiving a transducer lead therein;
   means for selectively venting said reference chamber to atmosphere;
   means for selectively providing a high resistance bleed path between said animal chamber and said reference chamber;
   a pneumotachograph in said animal chamber; and
   an aerosol manifold in said animal chamber for selectively distributing an aerosol in said animal chamber.

2. In the plethysmograph of claim 1, said aerosol manifold including a plurality of radially extending apertures which open into said animal chamber for evenly distributing said aerosol into said animal chamber.

3. In the plethysmograph of claim 1, said aerosol manifold being centrally located in a top wall of said animal chamber.

4. In the plethysmograph of claim 1, said means for selectively venting said animal chamber to atmosphere and said means for selectively venting said reference chamber to atmosphere comprising ports mounted in an outer wall of said respective chambers, said ports being movable between an open position and a closed position.

5. In the plethysmograph of claim 1, said means for providing a high resistance bleed path between said animal chamber and said reference chamber comprising a port, said port having a first end which is in communication with said animal chamber and a second end in communication with said reference chamber, said second end having an elongated length of tubing connected thereto, said tubing extending into the interior of said reference chamber.

6. In the plethysmograph of claim 1, said means for venting said animal chamber comprising four venting ports circumferentially spaced around said animal chamber, said venting ports being movable between open and closed positions.

7. The plethysmograph of claim 6 further comprising a second pneumotachograph, said pneumotachographs being radially aligned with two diametrically opposed venting ports.

8. A whole body plethysmograph comprising:
   a generally cylindrical container having an outer wall, top and bottom walls, and a bulkhead positioned intermediate said top and bottom walls, said bulkhead dividing said container into a lower animal chamber and an integral reference chamber positioned above said animal chamber;
   a port in said animal chamber for receiving a transducer lead therein;
   means for selectively venting said animal chamber to atmosphere;
   a port in said reference chamber for receiving a transducer lead therein;
   means for selectively venting said reference chamber to atmosphere;
   means for selectively providing a high resistance bleed path between said animal chamber and said reference chamber;
   a pneumotachograph in said animal chamber; and
   an aerosol manifold having an external end for receiving an aerosol from an aerosol source and an internal end which communicates with said animal chamber for distributing said aerosol in said animal chamber, said internal end of said aerosol manifold extending through said reference chamber, downwardly through said bulkhead, and opening into said animal chamber.

9. In the plethysmograph of claim 8, said internal end of said aerosol manifold including a plurality of radially directed apertures which open into said animal chamber for evenly distributing said aerosol into said animal chamber.

10. In the plethysmograph of claim 8, said aerosol manifold extending axially downwardly through said reference chamber.

11. In the plethysmograph of claim 8, said means for venting said animal chamber comprising four venting ports circumferentially spaced around said animal chamber, said venting ports being movable between open and closed positions.

12. The plethysmograph of claim 11 further comprising a second pneumotachograph, said pneumotachographs being radially aligned with two diametrically opposed venting ports.

* * * * *